United States Patent [19]

Berg et al.

[11] Patent Number: 4,654,123

[45] Date of Patent: Mar. 31, 1987

[54] DEHYDRATION OF ETHANOL BY EXTRACTIVE DISTILLATION

[76] Inventors: Lloyd Berg; An-I Yeh, both of 1314 S. Third Ave., Bozeman, Mont. 59715

[21] Appl. No.: 815,519

[22] Filed: Jan. 2, 1986

Related U.S. Application Data

[63] Continuation-in-part of Ser. No. 752,784, Jul. 8, 1985, abandoned.

[51] Int. Cl.⁴ .......................... B01D 3/40; C07C 29/84
[52] U.S. Cl. ......................................... 203/19; 203/51; 203/56; 203/58; 203/60; 203/61; 203/63; 203/64; 203/65; 203/71; 203/DIG. 13
[58] Field of Search ....................... 203/19, 18, 61, 58, 203/56, 63, 60, 51, 64, 65, 71, DIG. 13; 568/916; 435/161; 426/494

[56] References Cited

U.S. PATENT DOCUMENTS

| | | | |
|---|---|---|---|
| 1,796,059 | 3/1931 | Suida | 203/60 |
| 2,591,671 | 4/1952 | Catterall | 203/19 |
| 4,349,416 | 9/1982 | Brandt et al. | 203/19 |
| 4,366,032 | 12/1982 | Mikitenko et al. | 203/58 |
| 4,428,798 | 1/1984 | Zudkevitch et al. | 203/19 |
| 4,455,198 | 6/1984 | Zudkevitch et al. | 203/19 |
| 4,559,109 | 12/1985 | Lee et al. | 203/58 |

*Primary Examiner*—Wilbur Bascomb

[57] ABSTRACT

Water cannot be completely removed from ethanol by distillation because of the presence of the minimum azeotrope. Ethanol can be readily dehydrated by using extractive distillation in which the water is removed as overhead product and the ethanol and extractive agent as bottoms and subsequently separated by conventional rectification. Typical examples of suitable extractive agents are hexahydrophthalic anhydride; methyl tetrahydrophthalic anhydride and pentanol-1; trimellitic anhydride, ethyl salicylate and resorcinol.

5 Claims, No Drawings

DEHYDRATION OF ETHANOL BY EXTRACTIVE DISTILLATION

This application is a continuation-in-part of application Ser. No. 06/752,784 filed July 8, 1985 and now abandoned.

FIELD OF THE INVENTION

This invention relates to a method for separating water from ethanol using certain higher boiling liquids as the extractive agent in extractive distillation.

DESCRIPTION OF THE PRIOR ART

Extractive distillation is the method of separating close boiling compounds by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the overhead product. This usually requires that the extractive agent boil twenty Centigrade degrees or more higher than the lowest boiling component.

At the bottom of a continuous column, the less volatile components of the close mixtures and the extractive agent are continuously removed from the column. The usual methods of separation of these two components are the use of another rectification column, cooling and phase separation, or solvent extraction.

The separation of water from ethanol is one of the world's oldest technical problems. The fermentation of carbohydrates to ethanol typically produces a product, wine, with 14% ethanol. At that level, the bacteria die and fermentation ceases. Distillation of the wine will increase the ethanol content. There is a minimum azeotrope between water and ethanol however, containing 95.5% ethanol, 4.5% water and this limits the upper concentration of ethanol that can be obtained by rectification regardless of the number of theoretical plates employed.

In order to produce ethanol free of water, absolute alcohol, three general methods are employed. Distillation with a third component which forms a minimum azeotrope that boils lower than 78.15° C., the boiling point of the ethanol-water azeotrope. This can be a binary azeotrope such as water-ethyl ether, reported by Othmer & Wentworth, Ind. & Engr. Chem., 32, 1588 (1940), or a ternary azeotrope such as benzene-water-ethanol, well described in Kirk & Othmer, Encyclopedia of Chemical Technology. While the benzene-water-ethanol ternary is probably the most widely used method of dehydrating ethanol, these methods require a great deal of boiling and consequently a large heat requirement.

Removal of the water with a solid dehydrating agent is well known. Fresh quicklime, anhydrous calcium chloride, anhydrous calcium sulfate, fused anhydrous potassium acetate and sodium acetate, barium oxide and silica gel have been widely used. Barium oxide to react with the water to form barium hydroxide gets the last traces of water from ethanol. Silica gel is probably currently the most widely used. All of these reagents have the disadvantage in that they must be extensively treated to remove the water before they can be reused.

Extractive distillation is a third general method. The earliest application of extractive distillation to the dehydration of ethanol is probably Schneible, U.S. Pat. No. 1,469,447, Oct. 2, 1923 who used glycerine as the extractive agent. Smith & Carlson, U.S. Pat. No. 2,559,519, July 2, 1951 employed ethoxyethanol and butoxyethanol as the extractive agent and Catterall, U.S. Pat. No. 2,591,672, Apr. 8, 1952 reported gasoline as being effective. Drout & Dowling, French Pat. No. 1,020,351, Feb. 5, 1953 used glycols, glycol ethers or glycol esters as the extractive agent and Washall, U.S. Pat. No. 3,464,896, Sept. 2, 1969 dehydrated the higher alcohols using ethylene glycol as the extractive distillation agent. Catterall, U.S. Pat. No. 2,591,671 reported butyl, amyl and hexyl alcohols as extractive agents. Kirschenbaum, U.S. Pat. No. 2,901,404 investigated sulfuric acid, acetone or furfural as extractive distillation agents for dehydrating ethanol. Brandt, U.S. Pat. No. 4,349,416 described the use of ethylene glycol for this purpose. Mikitenko, U.S. Pat. No. 4,366,032 added ethanolamine and N-methyl pyrrolidone to the list of effective agents. Braithwaite, U.S. Pat. No. 4,400,241 reported the use of alkali-metal or alkaline-earth metal salts, sodium tetraborate dissolved in ethylene glycol and dipotassium phosphate dissolved in glycerol. Zudkevich, U.S. Pat. No. 4,428,798 and 4,455,198 described the use of 2-phenyl phenol, cumyl phenol, diisopropyl phenol, cyclohexyl cyclohexanone, phenyl cyclohexanone and cyclohexyl cyclohexanol as agents.

Extractive distillation typically requires the addition of an equal amount to twice as much extractive agent as the ethanol-water on each plate of the rectification column. The extractive agent should be heated to about the same temperature as the plate into which it is introduced. Thus extractive distillation imposes an additional heat requirement on the column as well as somewhat larger plates. However this is usually less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with ethanol otherwise it will form a two phase azeotrope with the ethanol in the recovery column and some other method of separation will have to be employed.

The two principal methods of producing the ethanol are by the fermentation of carbohydrates and the hydration of ethylene. Both methods are in aqueous solutions and so the separation of the ethanol from the reaction mixture in either case involves the formation of the ethanol-water azeotrope.

OBJECTIVE OF THE INVENTION

The object of this invention is to provide a process or method of extractive distillation that will enhance the relative volatility of ethanol and water in their separation in a rectification column. It is a further object of this invention to identify suitable extractive distillation agents which will eliminate the ethanol-water azeotrope and make possible the production of pure ethanol and water by rectification. It is a further object of this invention to identify compounds meeting the above constraints which will bring out the water in high purity as overhead and the water-free ethanol and the extractive agent as bottoms in a rectification column. A further object of this invention is to identify organic compounds which are stable, can be separated from ethanol by rectification with relatively few plates and can be recycled to the extractive distillation column and reused with little decomposition.

SUMMARY OF THE INVENTION

The objects of this invention are provided by a process of dehydrating ethanol which entails the use of certain oxygenated organic compounds as the agent in extractive distillation.

DETAILED DESCRIPTION OF THE INVENTION

We have discovered that cetain derivatives of phthalic anhydride will effectively accomplish the dehydration of ethanol when employed as the agent in extractive distillation. The difference between most of the agents reported in the current literature and the ones we have discovered is that ours force the water out the top of the column, not as an azeotrope accompanied with some azeotrope former but in the pure state.

TABLE 1

Relative Volatilities With Agents Containing Trimellitic Anhydride

| Extractive Agent(s) | Relative Volatility Concentration of Ethanol | | | |
|---|---|---|---|---|
| | 95% | 90% | 85% | 80% |
| Trimellitic anhydride (TMA), Ethyl salicylate | 2.10 | 1.09 | 0.82 | |
| TMA, Methyl p-hydroxy benzoate | 1.41 | 0.97 | 0.84 | |
| TMA, Ethyl salicylate, Catechol | 1.31 | 1.12 | | |
| TMA, Ethyl salicylate, Resorcinol | 1.75 | 1.20 | | |
| TMA, Ethyl salicylate, Hydroquinone | 1.22 | 1.20 | 1.00 | |
| TMA, Ethyl salicylate, Hexahydro phthalic anhydride | 1.90 | 0.93 | | |
| TMA, Hexahydro phthalic anhydride, Methyl p-OH benzoate | 1.22 | 0.91 | 0.77 | |
| TMA, Phthalic anhydride | 1.09 | 0.99 | 0.79 | |
| TMA, Pentanol-1, Resorcinol | 1.31 | 1.23 | 1.04 | |

TABLE 2

Relative Volatilities With Agents Containing Hydrogenated Phthalic Anhydride

| Extractive Agent(s) | Relative Volatility Concentration of Ethanol | | | |
|---|---|---|---|---|
| | 95% | 90% | 85% | 80% |
| Hexahydro phthalic anhydride (HHPA) | 1.40 | 1.13 | 0.92 | 0.73 |
| HHPA, Pentanol-1 | 2.13 | 1.56 | 1.14 | |
| HHPA, Hexanol-1 | 1.25 | 0.90 | 0.77 | |
| HHPA, 1,5 Pentanediol | 1.00 | 0.82 | | |
| HHPA, Ethyl salicylate | 2.12 | 1.38 | 0.99 | |
| HHPA, Ethyl benzoate, Resorcinol | 1.49 | 1.11 | 0.82 | |
| HHPA, Ethyl salicylate, Resorcinol | 1.44 | 1.43 | 1.11 | 0.93 |
| HHPA, Pentanol-1, Resorcinol | 1.46 | 1.05 | | |

TABLE 2-continued

Relative Volatilities With Agents Containing Hydrogenated Phthalic Anhydride

| Extractive Agent(s) | Relative Volatility Concentration of Ethanol | | | |
|---|---|---|---|---|
| | 95% | 90% | 85% | 80% |
| Methyl tetrahydro phthalic anhydride | 1.64 | 1.15 | 0.84 | |
| Methyl tetrahydro phthalic anhydride, Pentanol-1 | 1.23 | 1.04 | 0.98 | |

The successful compounds and mixtures are listed in Tables 1 and 2. Table 1 lists the extractive agents containing trimellitic anhydride; Table 2, hydrogenated phthalic anhydrides. These data are expressed in terms of the relative volatility of water to ethanol and were obtained in an Othmer type vapor-liquid equilibrium still. In Tables 1 and 2 the ratio of extractive agent to ethanol-water was 1:1. The four columns under concentration of ethanol are the relative volatilities at several different ethanol-water ratios. The 95% column is the azeotrope, 95% ethanol, 5% water. The 90% column is 90% ethanol, 10% water. 85% Ethanol, 15% water and 80% ethanol, 20% water are also listed for the same agents. In every case, the relative volatility decreases as the water concentration increases and it appears that below about 70% ethanol, 30% water, the system reverses, putting out ethanol as overhead and water-extractive agent as bottoms. This invention thus appears to be limited to ethanol that has been concentrated to at least 70% ethanol, 30% water.

TABLE 3

| Data From Run Made In Rectification Column | | | | |
|---|---|---|---|---|
| Time | | 50 min. | 90 min. | Average Value |
| Charge: | Water: 5% Ethanol: 95% | | | |
| Overhead: | Water | 13.1% | 13.9% | 13.5% |
| | Ethanol | 86.9% | 86.1% | 86.5% |
| Bottoms: | Water | 6.3% | 4.0% | 5.2% |
| | Ethanol | 93.7% | 96.0% | 94.8% |
| Relative Volatility: | | 1.20 | 1.35 | 1.26 |
| Agent: 50% Hexahydro phthalic anhydride + 50% 1-Pentanol Added at 58° C. & 20 ml/min. | | | | |

Table 3 presents the results of a run made in a 4.5 theoretical plate rectification column. The agent was a 50–50% mixture of hexahydrophthalic anhydride-1-pentanol. These data show that after 90 minutes of steady operation, the separation attains a relative volatility of 1.35. With no extractive agent, the relative volatility is 1.00 and no separation of water from ethanol can be accomplished.

In every case in Tables 1-3, the amount of extractive agent was approximately equal to the amount of ethanol-water. Where there are two or more compounds making up a mixture, the quantities of each compound were equal.

THE USEFULNESS OF THE INVENTION

The usefulness of this invention can be demonstrated by referring to the data presented in Tables 1-3. The agents listed these show that water can be removed from ethanol as the overhead product rather than as bottoms admixed with the extractive agent as is the case in most other extractive distillations. Since water is the compound with the highest heat of vaporization, 970 Btu/lb., and our process requires it to be vaporized only once instead of twice, this is a more heat efficient method of carrying out the dehydration of ethanol by extractive distillation. The stability and higher boiling points of the extractive distillation agents used are such that complete separation from ethanol and recycle is obtainable by simple distillation and the amount required for make-up is small.

WORKING EXAMPLES

EXAMPLE 1

Fifty grams of 95% ethanol and 50 grams of hexahydrophthalic anhydride were charged to an Othmer type vapor-liquid equilibrium still and refluxing carried out for five hours. Analyses of vapor and liquid by gas chromatography gave a relative volatility of 1.40. Three grams of water were added, refluxing continued for another four hours after which analyses of vapor and liquid gave a relative volatility of 1.13. Three more grams of water were added, refluxing continued for twelve hours, analyses indicated a relative volatility of 0.92. Three more grams of water were added, refluxed another twelve hours, analyses gave a relative volatility of 0.73. These data appear in Table 2.

EXAMPLE 2

Fifty grams of 95% ethanol, 25 grams of trimellitic anhydride (TMA) and 25 grams of ethyl salicylate were charged to the vapor-liquid equilibrium still and refluxed for twelve hours. Analyses of vapor and liquid indicated a relative volatility of 2.10. Three grams of water were added, refluxing continued for another four hours after which analyses indicated a relative volatility of 1.10. Three more grams of water were added, refluxing continued for another four hours and analyses then indicated a relative volatility of 0.82. These data are listed in Table 1.

EXAMPLE 3

Fifty grams of 95% ethanol, 17 grams of hexahydrophthalic anhydride, 17 grams of ethyl salicylate and 17 grams of resorcinol were charged to the vapor-liquid equilibrium still and refluxed for four hours. Analyses of vapor and liquid gave a relative volatility of 1.44. Three grams of water were added and refluxing continued for another seven hours after which analyses gave a relative volatility of 1.43. Three more grams of water were added, refluxed another eleven hours, analyses gave a relative volatility of 1.11. Three more grams of water were added, refluxed another five hours, analyses gave a relative volatility of 0.93. These data are listed in Table 2.

EXAMPLE 4

A glass perforated plate rectification column was calibrated with ethylbenzene and p-xylene which possesses a relative volatility of 1.06 and found to have 4.5 theoretical plates. 380 grams of ethanol and 20 grams of water was placed in the stillpot and heated. When refluxing began, on extractive agent comprising 50% hexahydrophthalic anhydride 50% 1-pentanol was pumped into the column at a rate of 20 ml/min. The temperature of the extractive agent as it entered the column was 58° C. After establishing the feed rate of the extractive agent, the heat input to the ethanol and water in the stillpot was adjusted to give a total reflux rate of 10-20 ml/min. After 50 minutes of operation, the overhead and bottoms samples of approximately two ml. were collected and analysed using gas chromatography. The overhead analysis was 13.1% water, 86.9% ethanol. The bottoms analysis was 6.3% water, 93.7% ethanol. Using these compositions in the Fenske equation, with the number of theoretical plates in the column being 4.5, gave an average relative volatility of 1.20 for each theoretical plate. After 1.5 hours of total operating time, the overhead and bottoms samples were again taken and analysed. The overhead composition was 13.9% water, 86.1% ethanol and the bottoms composition was 4.0% water, 96% ethanol. This gave an average relative volatility of 1.35 for each theoretical plate. These data are listed in Table 3.

We have shown that by the use of the proper compound or compounds as agents, ethanol can be effectively dehydrated by extractive distillation in which the water is removed as overhead product while the ethanol and the extractive agent come out as bottoms.

We claim:

1. A method for recovering anhydrous ethanol from a mixture of ethanol and water which comprises extractively distilling a mixture of ethanol and water containing not more than 30% water in a rectification column in the presence of about one part of extractive agent per part of ethanol-water mixture, recovering water as overhead product, obtaining the ethanol and the extractive agent from the stillpot, separating the ethanol from the extractive agent by distillation in another rectification column, wherein the extractive agent comprises hexahydrophthalic anhydride.

2. The method of claim 1 in which the extractive agent comprises hexahydrophthalic anhydride and at least one material from the group consisting of pentanol-1, hexanol-1, 1,5-pentanediol, ethyl salicylate and resorcinol.

3. A method for recovering anhydrous ethanol from a mixture of ethanol and water which comprises extractively distrilling a mixture of ethanol and water containing not more than 30% water in a rectification column in the presence of about one part of extractive agent per part of ethanol-water mixture, recovering water as overhead product, obtaining the ethanol and the extractive agent from the stillpot, separating the ethanol from the extractive agent by distillation in another rectification column, wherein the extractive agent comprises methyl tetrahydrophthalic anhydride.

4. The method of claim 3 in which the extractive agent comprises a mixture of methyl tetrahydrophthalic anhydride and pentanol-1.

5. A method for recovering anhydrous ethanol from a mixture of ethanol and water which comprises extractively distilling a mixture of ethanol and water containing not more than 30% water in a rectification column in the presence of about one part of extractive agent per part of ethanol-water mixture, recovering water as overhead product, obtaining the ethanol and the extractive agent from the stillpot, separating the ethanol from the extractive agent by distillation in another rectification column, wherein the extractive agent comprises trimellitic anhydride and at least one material from the group consisting of ethyl salicylate, methyl p-hydroxy benzoate, catechol, resorcinol, hydroquinone, hexahydrophthalic anhydride, phthalic anhydride and pentanol-1.

* * * * *